US010352682B2

(12) United States Patent
Yoshiya

(10) Patent No.: US 10,352,682 B2
(45) Date of Patent: Jul. 16, 2019

(54) DISPLACEMENT DETECTION DEVICE

(71) Applicant: MELEXIS TECHNOLOGIES SA, Bevaix (CH)

(72) Inventor: Takumi Yoshiya, Yokohama (JP)

(73) Assignee: MELEXIS TECHNOLOGIES SA, Bevaix (CH)

( * ) Notice: Subject to any disclaimer, the term of this patent is extended or adjusted under 35 U.S.C. 154(b) by 92 days.

(21) Appl. No.: 15/654,781

(22) Filed: Jul. 20, 2017

(65) Prior Publication Data
US 2018/0023941 A1   Jan. 25, 2018

(30) Foreign Application Priority Data
Jul. 20, 2016   (JP) ................. 2016-142449

(51) Int. Cl.
*G01B 7/14* (2006.01)
*G01B 7/02* (2006.01)
(Continued)

(52) U.S. Cl.
CPC ............. *G01B 7/023* (2013.01); *G01B 7/003* (2013.01); *G01B 7/14* (2013.01); *G01D 5/145* (2013.01); *G01N 27/72* (2013.01)

(58) Field of Classification Search
CPC .......... G01B 7/023; G01B 7/003; G01B 7/14; G01B 7/08; G01B 7/30; G01N 27/72;
(Continued)

(56) References Cited

U.S. PATENT DOCUMENTS 8,664,945 B2   3/2014 Laville et al.
2006/0279280 A1*  12/2006 Minamitani ........... G01R 33/09
324/252

(Continued)

FOREIGN PATENT DOCUMENTS

EP     1962062 A1   8/2008
GB     1416940      12/1975
(Continued)

OTHER PUBLICATIONS

European Search Report including European Search Opinion issued to the corresponding European application No. 17182258.8 dated Dec. 1, 2017.

*Primary Examiner* — Thang X Le
(74) *Attorney, Agent, or Firm* — Hauptman Ham, LLP

(57) ABSTRACT

Provided is a displacement detection device which reduces the influence of disturbance noise on a magnetic field to be detected and makes a range detectable by a monopole magnet wider than a pitch of a magnetic detection elements. A displacement detection device includes a magnet which is displaced in a displacement direction $D_s$, is rod-shaped and has a form in which a longitudinal direction and the displacement direction $D_s$ form a predetermined angle θ, and a sensor IC in which magnetic detection element groups, which detect a magnetic flux density of a magnetic field formed by the magnet in an x direction and a z direction orthogonal to the displacement direction $D_s$, are arranged in pairs with a predetermined interval $d_p$, and which outputs a difference between outputs of the magnetic detection element groups.

13 Claims, 20 Drawing Sheets

(51) Int. Cl.
*G01B 7/00* (2006.01)
*G01D 5/14* (2006.01)
*G01N 27/72* (2006.01)

(58) Field of Classification Search
CPC ............ G01D 5/16; G01D 5/20; G01D 5/142; G01D 5/145; G01D 5/147; G01D 5/04; G01D 5/12; G01R 33/093; G01R 33/098; G01R 33/0011
See application file for complete search history.

(56) References Cited

U.S. PATENT DOCUMENTS

| | | | |
|---|---|---|---|
| 2007/0273365 A1 | 11/2007 | Lanter et al. | |
| 2008/0265877 A1* | 10/2008 | Kato | G01D 5/245 324/207.25 |
| 2009/0045807 A1* | 2/2009 | Nishida | G01D 5/145 324/207.2 |
| 2009/0177436 A1 | 7/2009 | Yoshida et al. | |
| 2013/0314079 A1* | 11/2013 | Suzuki | G01D 5/145 324/207.25 |
| 2015/0137796 A1* | 5/2015 | Ausserlechner | G01B 7/30 324/207.2 |
| 2015/0142376 A1* | 5/2015 | Ausserlechner | G01D 5/145 702/151 |

FOREIGN PATENT DOCUMENTS

| | | |
|---|---|---|
| JP | 2011-257432 A | 12/2011 |
| JP | 2014-190711 A | 10/2014 |

* cited by examiner

DISPLACEMENT DETECTION DEVICE

The present application is based on Japanese patent application No. 2016-142449, the entire contents of which are incorporated herein by reference.

BACKGROUND OF THE INVENTION

Field of the Invention

One embodiment of the invention relates to a displacement detection device.

Description of the Related Art

As a conventional technique, a displacement detection device, which detects a change of a magnetic field according to displacement of a detection target by using a differential magnetic detection element to reduce the influence of disturbance noise and detects displacement of the detection target, has been suggested (refer to Japanese Unexamined Patent Publication No. 2011-257432).

The displacement detection device in the referred document has a magnet and first and second sensor devices. The magnet has a magnetic multipole line. The first and second sensor devices move parallel to the surface of the magnetic multipole line of the magnet, constitute a bridge circuit and detect a position based on a signal outputted from the circuit according to the displacement. Since this displacement detection device uses the magnet having the magnetic multipole line as the detection target to expand a magnetic field range formed by the detection target, a displacement range detectable by the magnetic detection element can be made wider than a pitch of the magnetic detection element.

However, the displacement detection device in the referred document has a problem that the cost is increased because the magnet having the magnetic multipole line, which is more expensive than a monopole magnet, is required to be used.

BRIEF DESCRIPTION OF THE SEVERAL VIEWS OF THE DRAWINGS

A general architecture that implements the various features of the invention will now be described with reference to the drawings. The drawings and the associated descriptions are provided to illustrate embodiments of the invention and not to limit the scope of the invention.

DETAILED DESCRIPTION OF THE PREFERRED EMBODIMENT

Various embodiments according to the invention will be described hereinafter with reference to the accompanying drawings. In general, according to one embodiment of the invention, there is provided a displacement detection device, including:

a magnet which is displaced in one direction, is rod-shaped and has a form in which a longitudinal direction and the one direction form a predetermined angle; and a sensor in which magnetic detection element groups, which detect a magnetic flux density of a magnetic field formed by the magnet in a direction orthogonal to the one direction, are arranged in pairs with a predetermined interval, and which outputs a difference between outputs of the magnetic detection element groups.

According to the invention, it is possible to reduce the influence of disturbance noise on the magnetic field to be detected as well as make a range detectable by a monopole magnet wider than a pitch of the magnetic detection elements.

Hereinafter, embodiments of the invention will be described in detail with reference to the accompanying drawings.

First Embodiment (Configuration of Displacement Detection Device)

Figure 1:
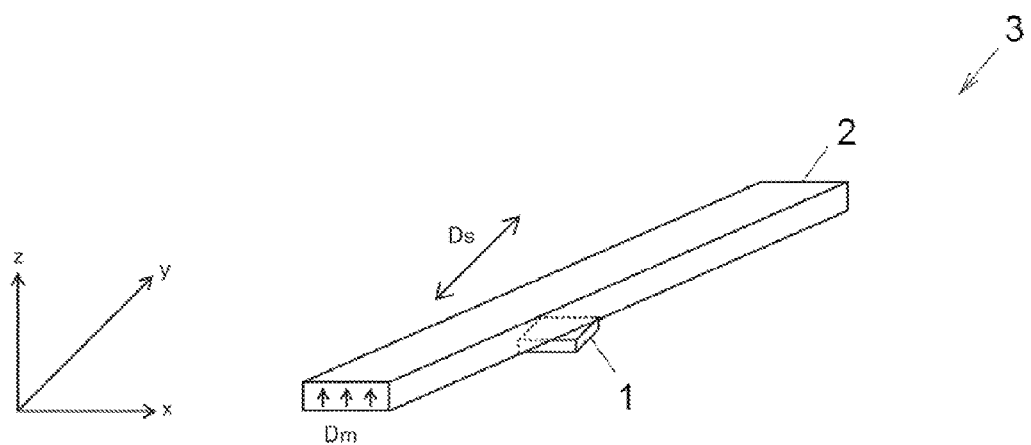
FIG. 1 is an exemplary perspective view showing a configuration example of a displacement detection device according to the first embodiment.
Figure 2A:
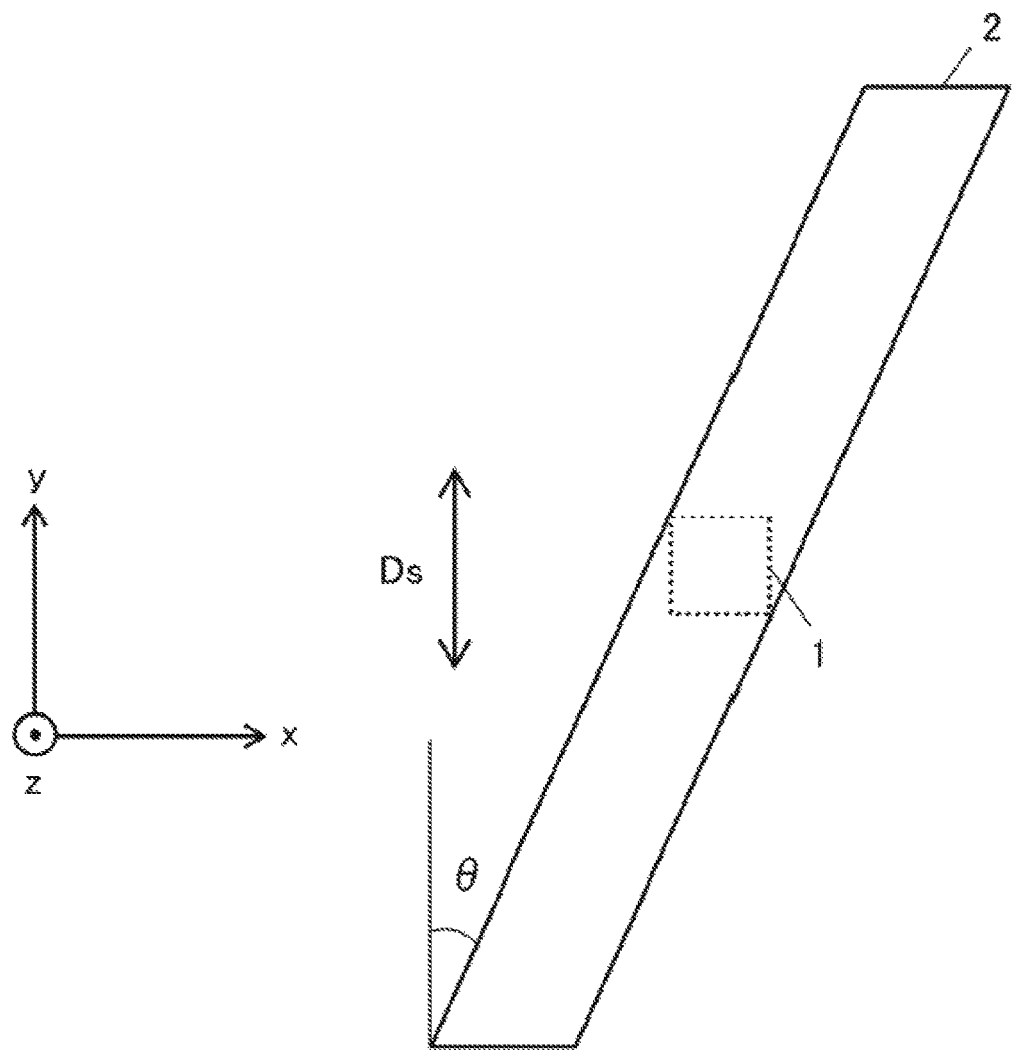
FIG. 2A and FIG. 2B are an exemplary plan view and a side view showing the configuration of the displacement detection device, respectively.
Figure 2B:
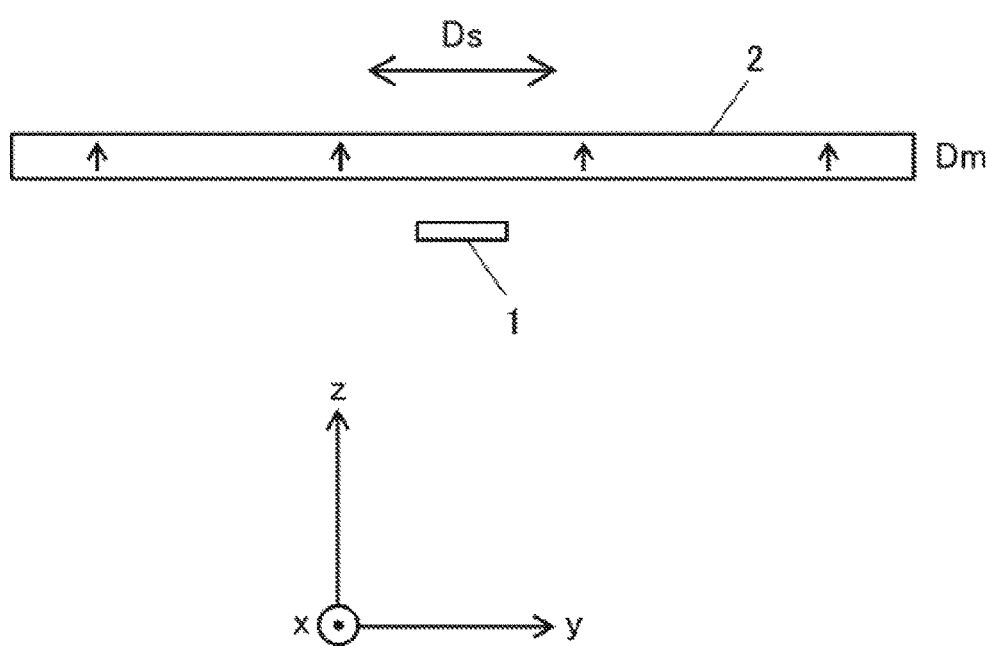

FIG. 1 is a perspective view showing a configuration example of a displacement detection device according to the first embodiment. FIG. 2A and FIG. 2B are a plan view and a side view showing the configuration of the displacement detection device, respectively.

A displacement detection device 3 has a sensor IC 1 and a magnet 2 arranged to face a magnetic detection surface of the sensor IC 1.

As will be described later, the sensor IC 1 is a magnetic sensor IC which detects magnetic flux densities by a plurality of Hall elements and differentially outputs voltages proportional to the respective magnetic flux densities in an x direction and a z direction.

The magnet 2 is a permanent magnet formed by using a material such as ferrite, samarium cobalt or neodymium, in which a direction parallel to a z axis is set as a magnetization direction Dm, and a direction parallel to a y axis is set as a displacement direction Ds. Moreover, the magnet 2 is inform that is tilted by a predetermined angle θ in the displacement direction Ds. As one example, a width in the x direction is set to 3 mm, a length in the y direction is set to 20 mm, and a thickness in the z direction is set to 5 mm.

Note that the magnet 2 only needs to be displaced relatively against the sensor IC 1 so that the sensor IC 1 may be displaced while the magnet 2 is fixed, or both may be displaced together.

The sensor IC 1 and the magnet 2 are arranged in the z direction with a predetermined interval, for example, 3 mm apart.

Figure 3A:
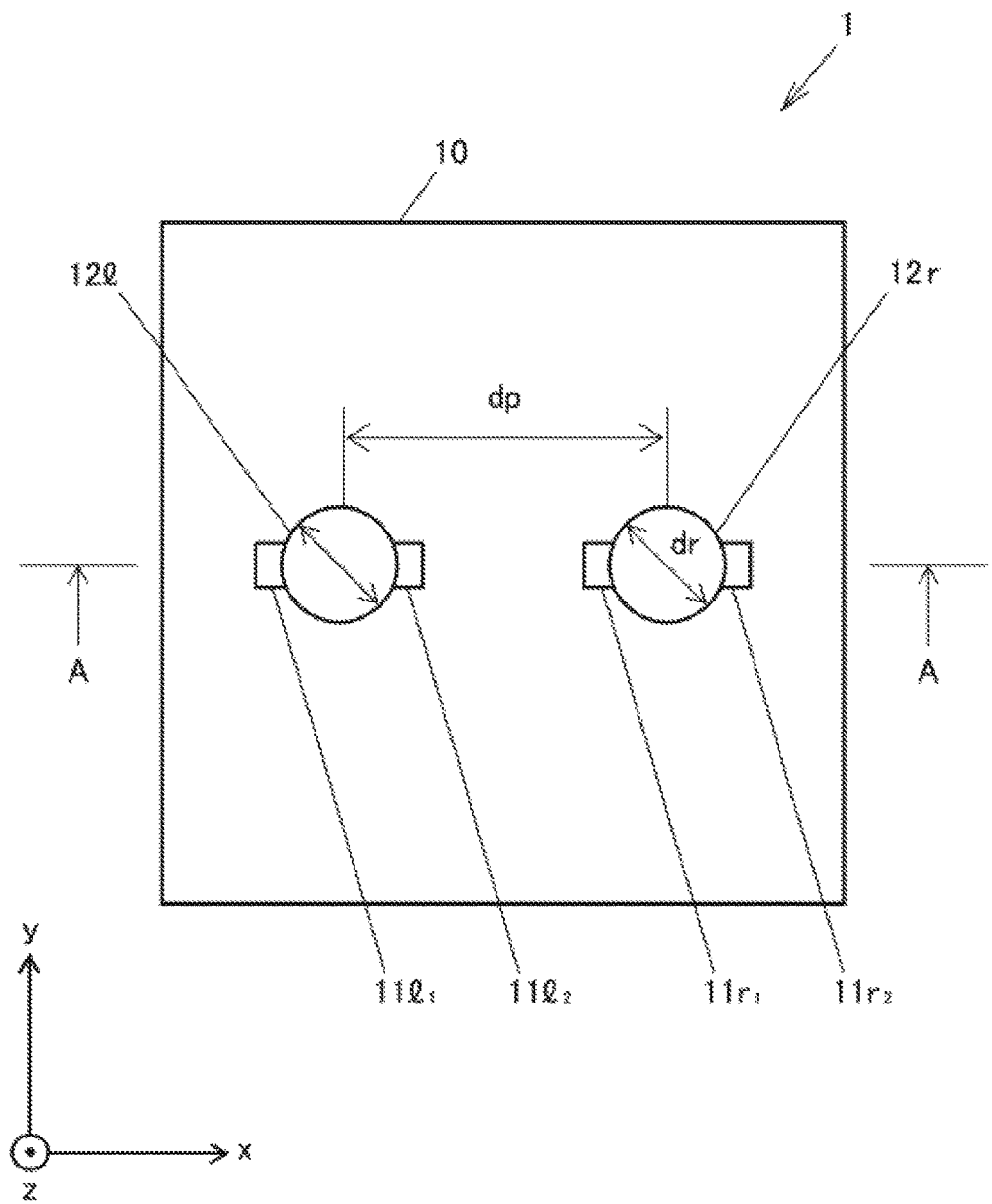
FIG. 3A and FIG. 3B are an exemplary plan view and a side view showing one example of the configuration of a sensor IC, respectively.
Figure 3B:
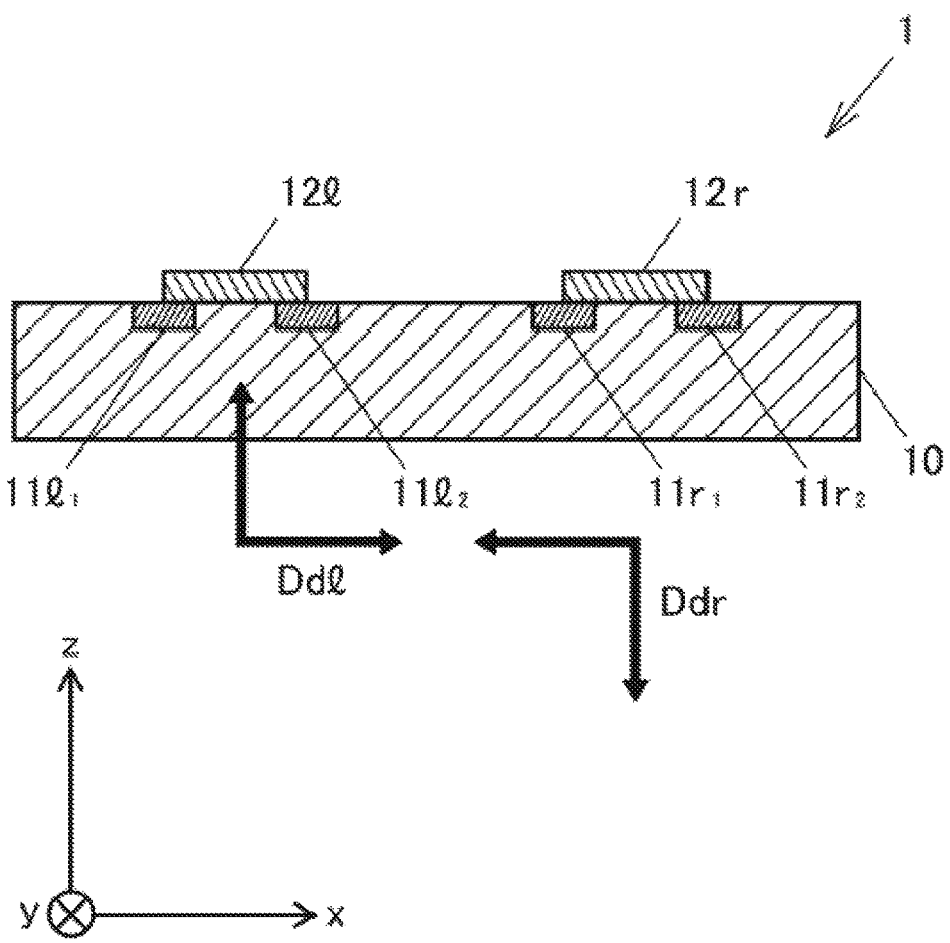

FIG. 3A and FIG. 3B are a plan view and an A-A cross-sectional view showing one example of the configuration of the sensor IC 1, respectively.

As shown in FIG. 3A and FIG. 3B, the sensor IC 1 includes, as one example, a flat substrate 10 having a thickness in the z direction, Hall elements $11_{l1}$, $11_{l2}$, $11_{r1}$ and $11_{r2}$ which are provided on the substrate 10, have detection surfaces parallel to an xy plane, and serve as magnetic detection elements whose detection direction is set to the z direction, magnetic concentrators (IMC) $12_l$ and $12_r$ which are provided so as to partially overlie the Hall elements $11_{l1}$, $11_{l2}$, $11_{r1}$ and $11_{r2}$, and convert a magnetic flux in the x direction into the z direction to be detected by the Hall elements $11_{l1}$, $11_{l2}$, $11_{r1}$ and $11_{r2}$, and signal processing circuits (FIG. 5 and FIG. 6) which process signals outputted by the Hall elements $11_{l1}$, $11_{l2}$, $11_{r1}$ and $11_{r2}$, and is a Hall IC which detects the magnetic flux densities in the x and z directions. Note that a magnetic flux density in the y direction may be detected by further arranging Hall elements in the y direction.

For example, by using the MLX 90371 sensor manufactured by Melexis or the like, the sensor IC 1 computes outputs of the Hall elements $11_{l1}$ and $11_{l2}$, which are a Hall elements group, to set a sensitive direction $D_{dl}$ to the x direction and z direction and computes outputs of the Hall elements $11_{r1}$ and $11_{r2}$, which are a Hall element group, so that an output proportional to a magnetic flux density of a sensitive direction $D_{dr}$ in the −x direction and −z direction can be obtained. The relationships between the magnetic flux densities and the outputs will be described later. Meanwhile, an interval between the Hall elements $11_{l1}$ and $11_{l2}$ and an interval $d_r$ between the Hall elements $11_{r1}$ and $11_{r2}$ are substantially equal to the diameters of the IMCs $12_l$ and $12_r$, respectively, $d_r=0.2$ mm, and an interval $d_p$ between the IMCs $12_l$ and $12_r$ is $d_p=1.8$ to $1.9$ mm. Moreover, the sensor IC 1 has a thickness of 40 μm in the z direction, a width of 2500 μm in the x direction, and a width of 2000 μm in the y direction. Note that Permalloy can be used as the IMC 12 of the sensor IC 1.

Note that, for the sensor IC 1, a different kind of elements such as an MR element may be used as long as the detection direction of each Hall element group is the x direction and the z direction and an output is obtained by a differential output of each Hall element group, or a multi-axial magnetic detection IC, in which magnetic detection elements are arranged in a plurality of respective axial directions, may be used as long as the detection direction includes the x direction and the z direction.

(Operation of Displacement Detection Device)

Next, the action of the first embodiment will be described using FIG. 1 to FIG. 9.

(Operation of Sensor IC)

Figure 4:
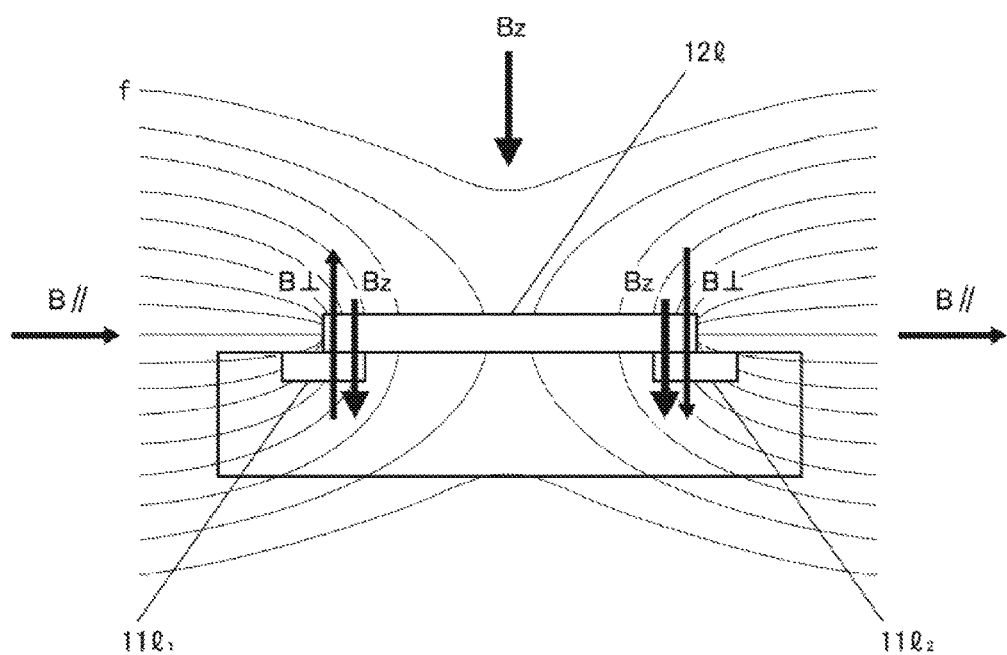
FIG. 4 is an exemplary schematic view for explaining the operation of the sensor IC of the displacement detection device.

FIG. 4 is a schematic view for explaining the operation of the sensor IC 1 of the displacement detection device 3. Illustrated is a magnetic flux detected by the Hall elements $11_{l1}$ and $11_{l2}$ which are the left Hall element group, and the same applies to a magnetic flux detected by the Hall elements $11_{r1}$ and $11_{r2}$ which are the right Hall element group.

The magnetic flux passing through the sensor IC 1 is sensed by the Hall elements $11_{l1}$ and $11_{l2}$, and a signal with a voltage proportional to the magnetic flux density is outputted.

A parallel component B// of the magnetic flux f is induced by the IMC 12 so that the magnitude of the magnetic flux density is converted into a vertical component B⊥ proportional to the parallel component B// and is sensed by the Hall elements $11_{l1}$ and $11_{l2}$. A vertical component $B_z$ is also sensed by the Hall elements $11_{l1}$ and $11_{l2}$.

In other words, the Hall element $11_{l1}$ on the left side of the drawing senses "B⊥-$B_z$," while the Hall element $11_{l2}$ on the right side of the drawing senses "−B⊥-$B_z$."

Therefore, by calculating a difference between the output of the Hall element $11_{l1}$ and the output of the Hall element $11_{l2}$, a signal with a voltage proportional to 2B⊥ can be obtained. In addition, by calculating the sum, a signal with a voltage proportional to −2Bz can be obtained.

Figure 5:
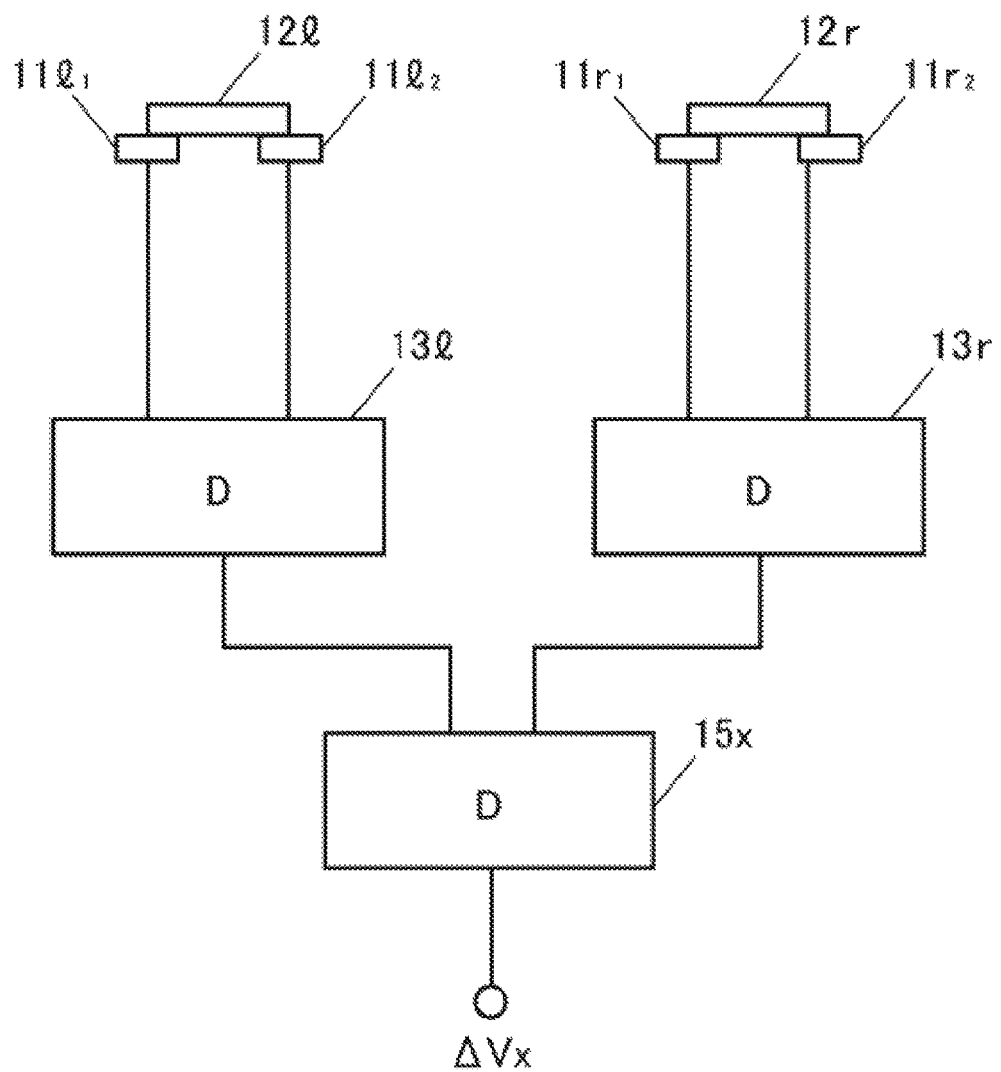
FIG. 5 is an exemplary schematic diagram showing a circuit when the sensor IC obtains an output $\Delta V_x$.

FIG. 5 is a schematic diagram showing a circuit when the sensor IC 1 obtains an output proportional to an x component of the magnetic field. Furthermore, FIG. 6 is a schematic diagram showing a circuit when the sensor IC 1 obtains an output proportional to a z component of the magnetic field.

As shown in FIG. 5, a differential circuit $13_l$ outputs an output difference between the Hall elements $11_{l1}$ and $11_{l2}$ which are the left Hall element group and outputs a voltage proportional to 2B⊥, which is the x component of the magnetic flux density, as described above. Similarly, a differential circuit $13_r$ outputs an output difference between the Hall elements $11_{r1}$ and $11_{r2}$ which are the right Hall element group and outputs a voltage proportional to 2B⊥, which is the x component of the magnetic flux density, as described above.

Next, a differential circuit $15_x$ outputs a voltage $\Delta V_x$ proportional to an output difference between the differential circuits $13_l$ and $13_r$, that is, $\Delta B_x$ which is a difference between the x component of the magnetic flux density detected by the left Hall element group and the x component of the magnetic flux density detected by the right Hall element group.

Figure 6:
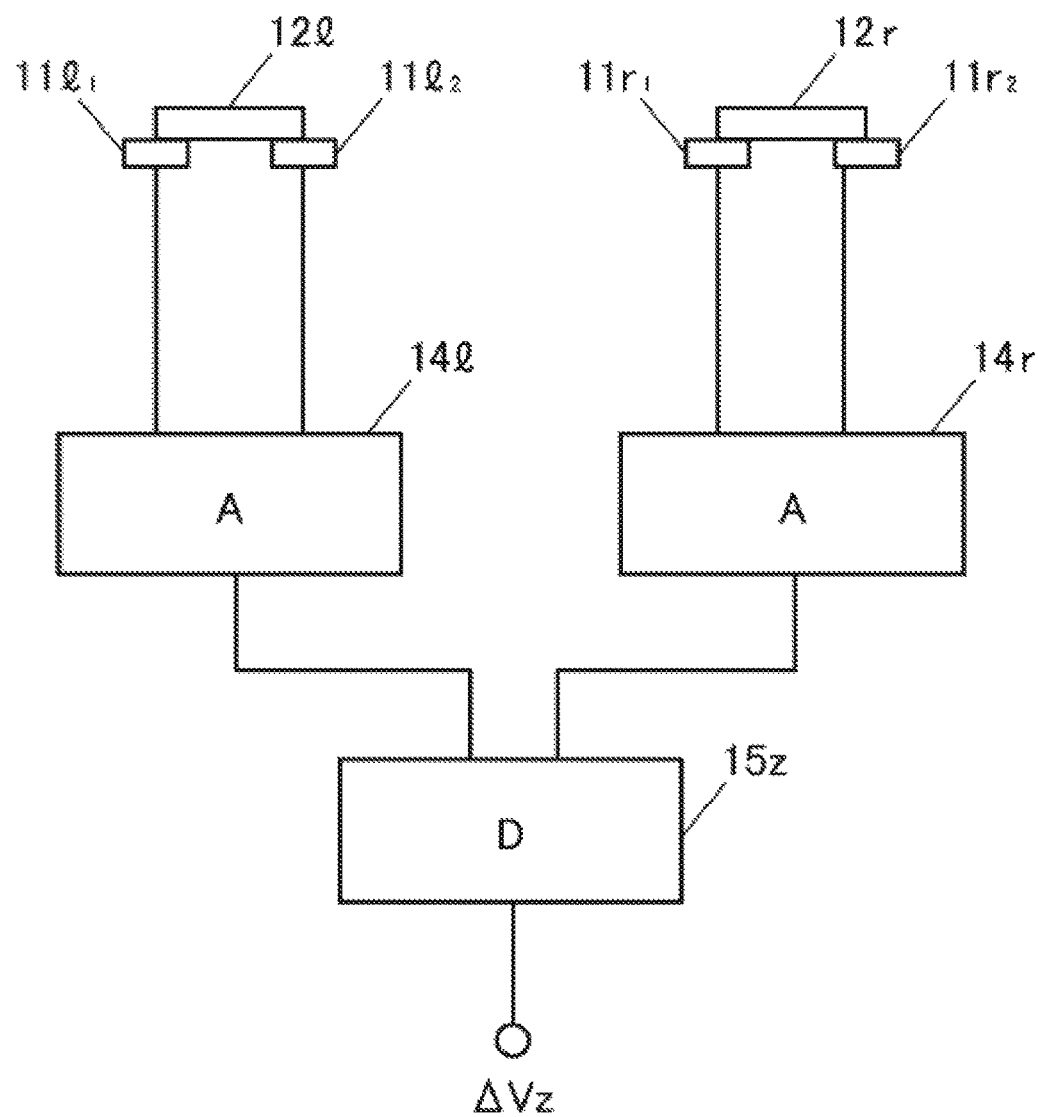
FIG. 6 is an exemplary schematic diagram showing a circuit when the sensor IC obtains an output $\Delta V_z$.

Moreover, as shown in FIG. 6, an adder circuit $14_l$ outputs the sum of the outputs of the Hall elements $11_{l1}$ and $11_{l2}$ which are the left Hall element group and outputs a voltage proportional to −2Bz, which is the z component of the magnetic flux density, as described above. Similarly, an adder circuit $14_r$ outputs the sum of the outputs of the Hall elements $11_{r1}$ and $11_{r2}$ which are the right Hall element group and outputs a voltage proportional to −2Bz, which is the z component of the magnetic flux density, as described above.

Next, a differential circuit $15_z$ outputs a voltage $\Delta V_z$ proportional to an output difference between the adder circuits $14_l$ and $14_r$, that is, $\Delta B_z$ which is a difference between the z component of the magnetic flux density detected by the left Hall element group and the z component of the magnetic flux density detected by the right Hall element group.

Note that FIG. 5 and FIG. 6 described above are for explaining the circuit configuration of the sensor IC 1, and the outputs of the Hall elements $11_{l1}$, $11_{l2}$, $11_{r1}$, and $11_{r2}$ may be processed by an analog circuit, or the outputs may be sequentially acquired by the DEMUX to be processed by a digital circuit.

(Relationships Between Displacement of Magnet and Output Values)

Figure 7A:
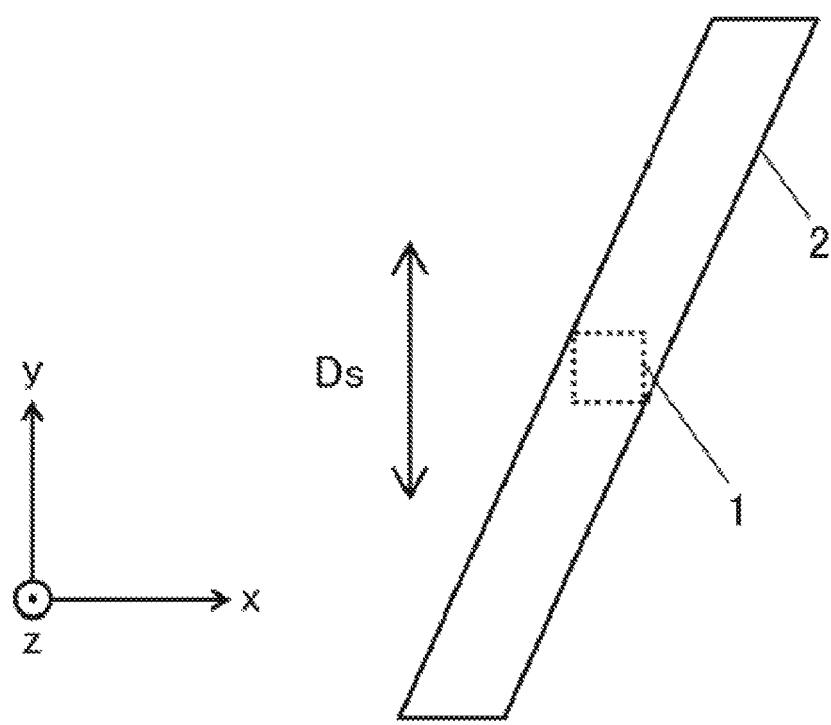
FIG. 7A to FIG. 7C are an exemplary schematic plan view showing displacement of a magnet, an exemplary schematic front view showing a state of a magnetic field formed by the magnet, and an exemplary graph showing output values outputted from differential circuits, respectively.
Figure 7B:
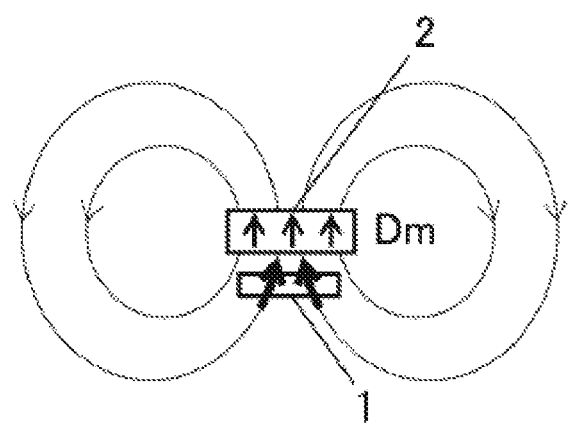
Figure 7C:
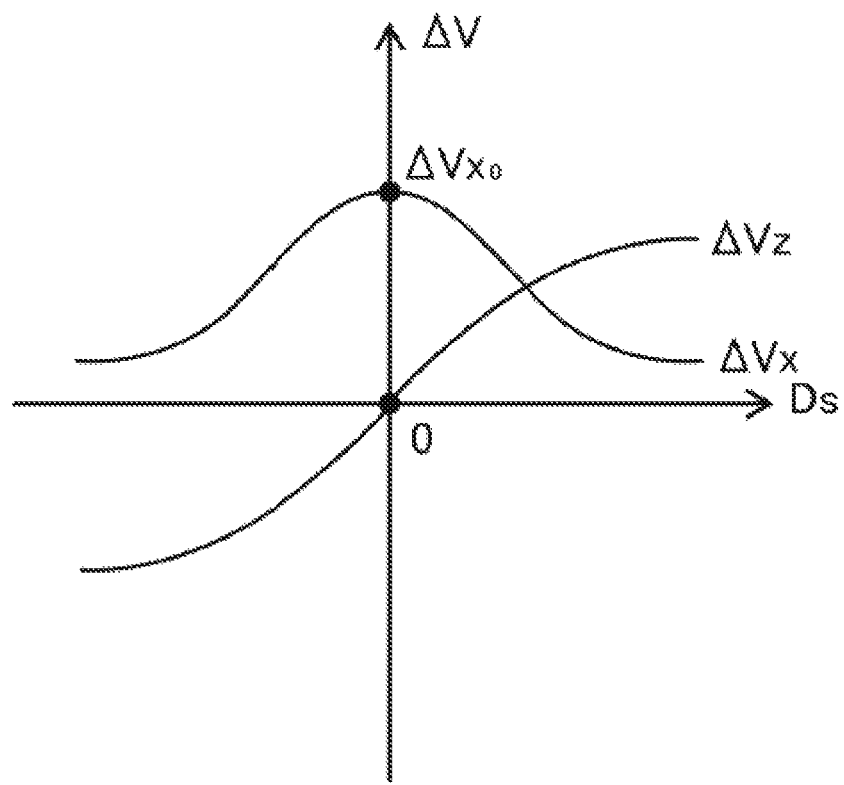

FIG. 7A to FIG. 7C are a schematic plan view showing the displacement of the magnet 2, a schematic front view showing the state of the magnetic field formed by the magnet 2, and a graph showing the output values outputted from the differential circuits $15_x$ and $15_z$, respectively.

When the sensor IC 1 and the magnet 2 are not displaced relatively to each other as shown in FIG. 7A, the magnet 2 is positioned right above the sensor IC 1 as shown in FIG. 7B.

In this case, the left Hall element group of the sensor IC 1 detects a magnetic flux density having a positive value in the x direction and a positive value in the z direction, while the right Hall element group detects a magnetic flux density having a negative value in the x direction and a positive value in the z direction. The absolute values of the magnetic flux densities in the x direction detected by the respective Hall element groups are the same, and the absolute values of the magnetic flux densities in the z direction detected by the respective Hall element groups are the same. Therefore, as shown in FIG. 7C, the output value $\Delta V_x$, which is outputted from the differential circuit $15_x$ and proportional to $\Delta B_x$, becomes the maximum value $\Delta V_{x0}$, and the output value $\Delta V_z$, which is outputted from the differential circuit $15_z$ and proportional to $\Delta B_z$, becomes 0.

Figure 8A:
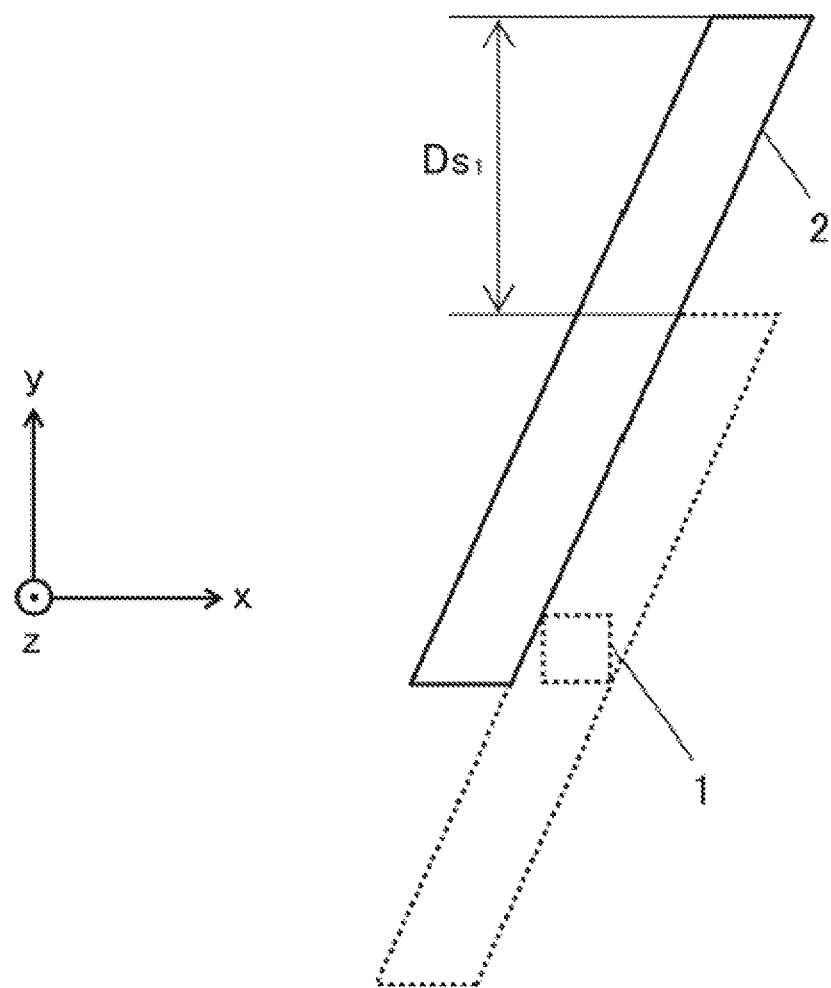
FIG. 8A to FIG. 8C are an exemplary schematic plan view showing displacement of a magnet, an exemplary schematic front view showing a state of a magnetic field formed by the magnet, and an exemplary graph showing output values outputted from differential circuits, respectively.
Figure 8B:
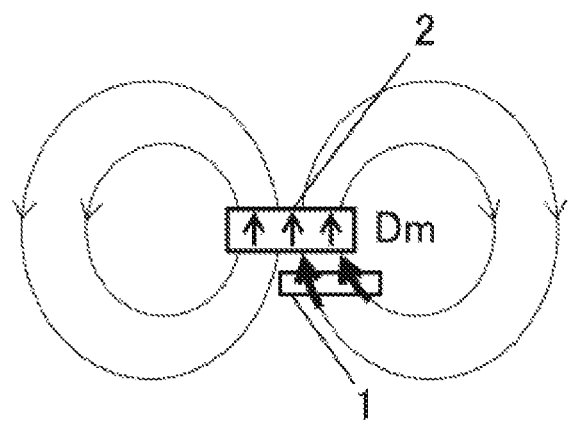
Figure 8C:
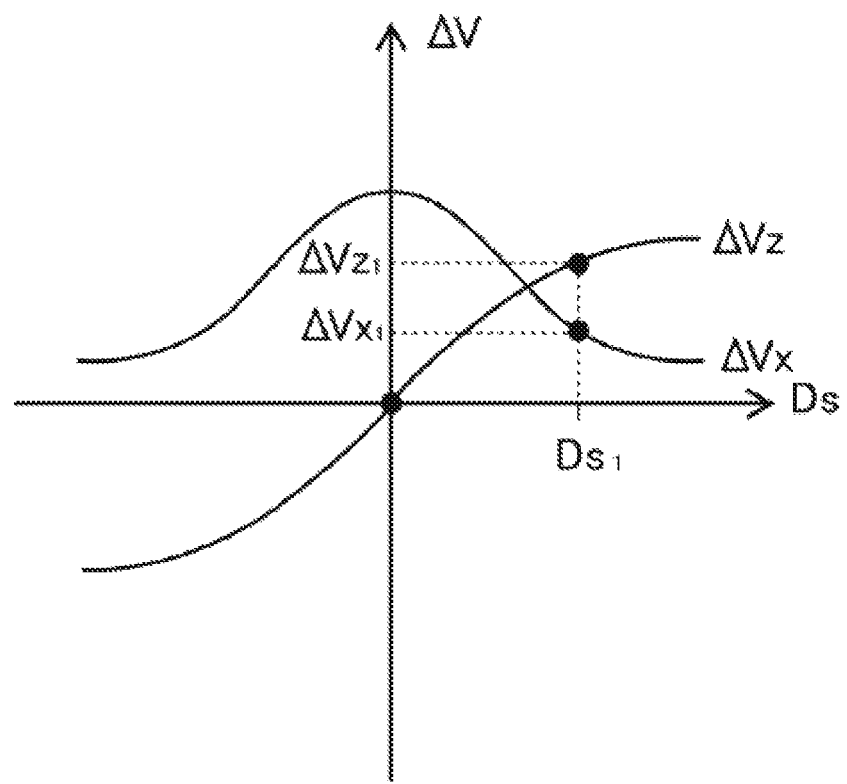

FIG. 8A to FIG. 8C are a schematic plan view showing the displacement of the magnet 2, a schematic front view showing the state of the magnetic field formed by the magnet 2, and a graph showing the output values outputted from the differential circuits $15_x$ and $15_z$, respectively.

When the sensor IC 1 and the magnet 2 are displaced relatively by only $D_{s1}$ as shown in FIG. 8A, the magnet 2 is positioned to the left side in the drawing above the sensor IC 1 as shown in FIG. 8B.

In this case, the left Hall element group of the sensor IC 1 detects a magnetic flux density having a negative value in the x direction and a positive value in the z direction, while the right Hall element group detects a magnetic flux density having a negative value in the x direction and a positive value in the z direction. The absolute value of the magnetic flux density in the x direction detected by the right Hall element group is larger than that detected by the left Hall element group, and the absolute value of the magnetic flux density in the z direction detected by the right Hall element group is smaller than that detected by the left Hall element group. Therefore, as shown in FIG. 8C, the output value $\Delta V_x$, which is outputted from the differential circuit $15_x$ and proportional to $\Delta B_x$, becomes $\Delta V_{x1}$, and the output value $\Delta V_z$, which is outputted from the differential circuit $15_z$ and proportional to $\Delta B_z$, becomes $\Delta V_{z1}$.

Figure 9A:
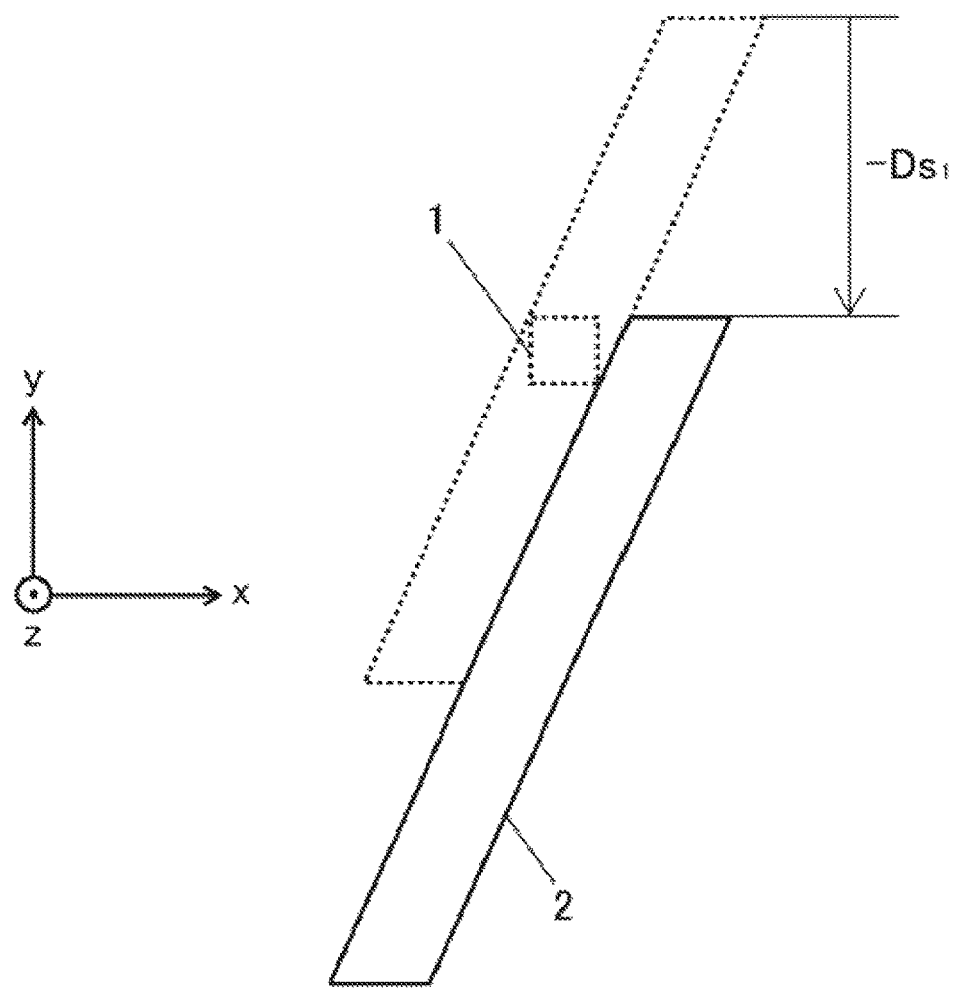
FIG. 9A to FIG. 9C are an exemplary schematic plan view showing displacement of a magnet, an exemplary schematic front view showing a state of a magnetic field formed by the magnet, and an exemplary graph showing output values outputted from differential circuits, respectively.
Figure 9B:
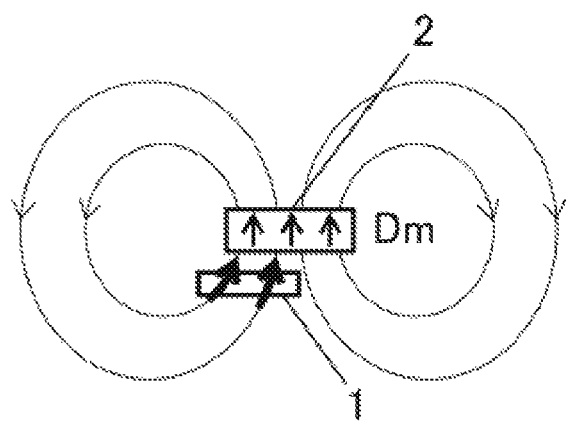
Figure 9C:
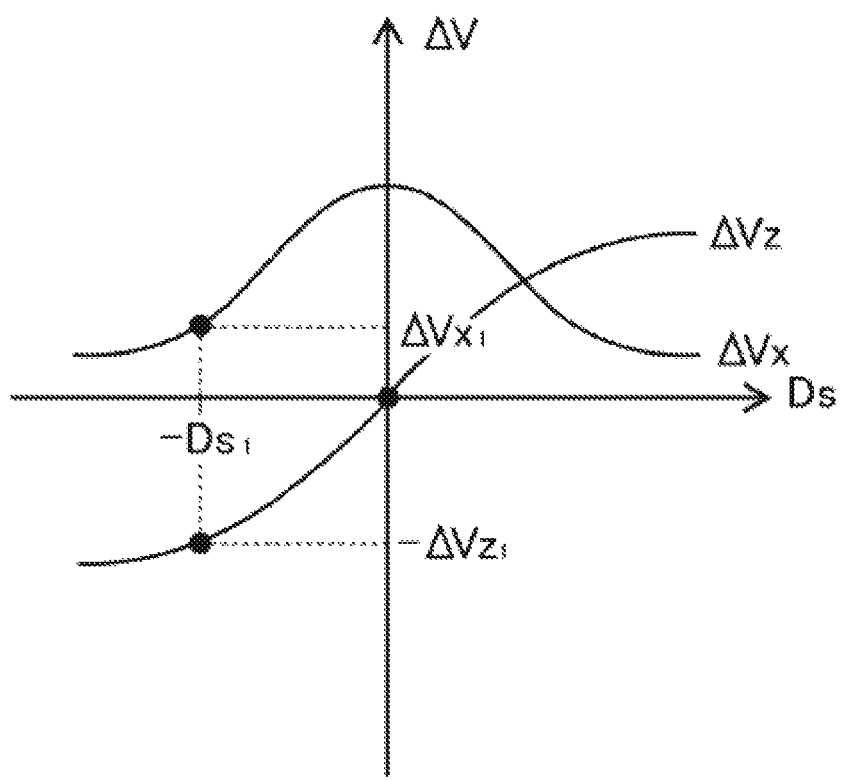

FIG. 9A to FIG. 9C are a schematic plan view showing the displacement of the magnet 2, a schematic front view showing the state of the magnetic field formed by the magnet 2, and a graph showing the output values outputted from the differential circuits $15_x$ and $15_z$, respectively.

When the sensor IC 1 and the magnet 2 are displaced relatively by only $D_{s1}$ as shown in FIG. 9A, the magnet 2 is positioned to the right side in the drawing above the sensor IC 1 as shown in FIG. 9B.

In this case, the left Hall element group of the sensor IC 1 detects a magnetic flux density having a positive value in the x direction and a positive value in the z direction, while the right Hall element group detects a magnetic flux density having a positive value in the x direction and a positive value in the z direction. The absolute value of the magnetic flux density in the x direction detected by the right Hall element group is smaller than that detected by the left Hall element group, and the absolute value of the magnetic flux density in the z direction detected by the right Hall element group is larger than that detected by the left Hall element group. Therefore, as shown in FIG. 9C, the output value $\Delta V_x$, which is outputted from the differential circuit $15_x$ and proportional to $\Delta B_x$, becomes $\Delta V_{x1}$, and the output value $\Delta V_z$, which is outputted from the differential circuit $15_z$ and proportional to $\Delta B_z$, becomes $-\Delta V_{z1}$.

Advantages of the First Embodiment

According to the first embodiment described above, the influence of disturbance noise on the magnetic field to be detected is reduced by using the sensor IC 1 which differentially detects changes of the magnetic fluxes, and a detectable range of the displacement can be made wider than a pitch $d_p$ of the magnetic detection elements even though a monopole magnet is used since the magnet 2 is arranged on the sensor IC 1 in a form that the magnet 2 is tilted by a predetermined angle $\theta$ in the displacement direction Ds.

That is, although the displacement range of the magnet detectable by the sensor IC 1 is normally about $d_p$ when a differential sensor IC 1 is used and the displacement direction of the magnet is set to the x direction, by using the magnet 2, a value obtained by multiplying the displacement in the displacement direction Ds by $\tan \theta$ becomes the displacement in the x direction. Thus, the displacement range of the magnet 2 detectable by the sensor IC 1 becomes $d_p/\tan \theta$ in the y direction, and a larger displacement can be detected as the value of $\theta$ becomes smaller.

Second Embodiment

The second embodiment is different from the first embodiment in that the magnetization direction Dm of the magnet of the first embodiment is set to be parallel to the x axis. Note that the same reference signs are used for the elements common to the first embodiment.

Figure 10:
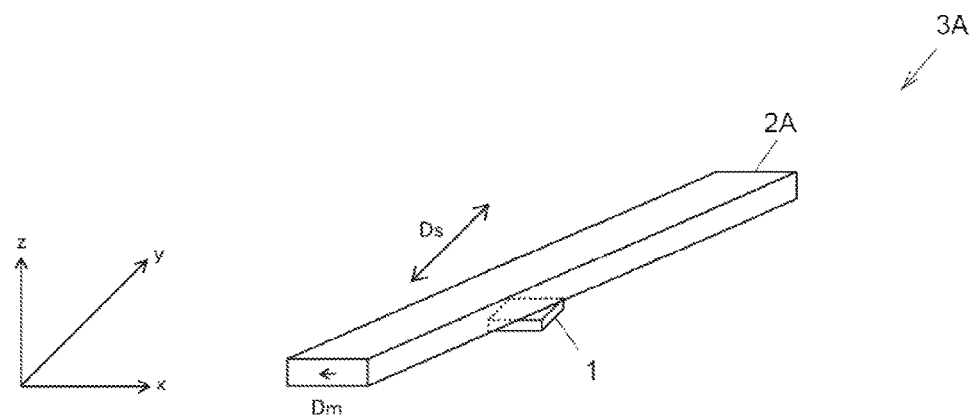
FIG. 10 is an exemplary perspective view showing a configuration example of a displacement detection device according to the second embodiment.

FIG. 10 is a perspective view showing a configuration example of a displacement detection device according to the second embodiment.

A displacement detection device 3A has a sensor IC 1 and a magnet 2A arranged above the sensor IC 1.

Like the magnet 2, the magnet 2A is a permanent magnet formed by using a material such as ferrite, samarium cobalt or neodymium, in which a direction parallel to an x axis is set as a magnetization direction Dm and a direction parallel to a y axis is set as a displacement direction Ds. Moreover, the magnet 2 is in form that is tilted by a predetermined angle $\theta$ in the displacement direction Ds. As one example, a width in the x direction is set to 3 mm, a length in the y direction is set to 20 mm, and a thickness in a z direction is set to 5 mm.

Note that the magnet 2 only needs to be displaced relatively against the sensor IC 1 so that the sensor IC 1 may be displaced, or both may be displaced.

The sensor IC 1 and the magnet 2 are arranged in the z direction with a predetermined interval, for example, 3 mm apart.

(Operation of Displacement Detection Device)

Next, the action of the second embodiment will be described using FIGS. 10 and 11.

Figure 11A:
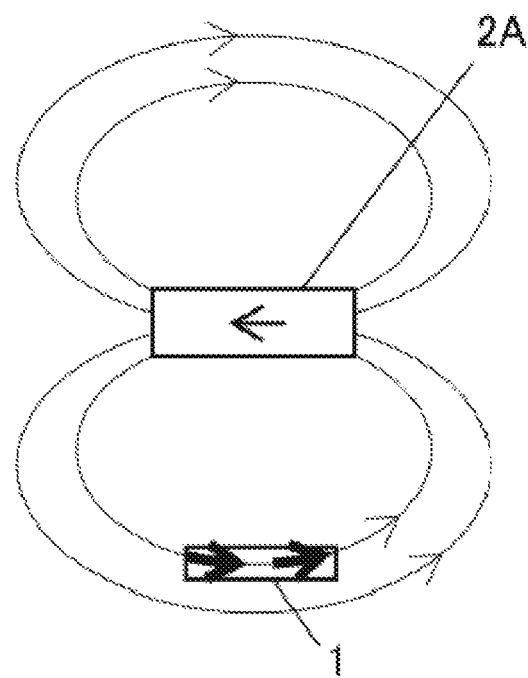
FIG. 11A and FIG. 11B are an exemplary schematic front view showing a state of a magnetic field formed by a magnet and an exemplary graph showing output values outputted from differential circuits, respectively.
Figure 11B:
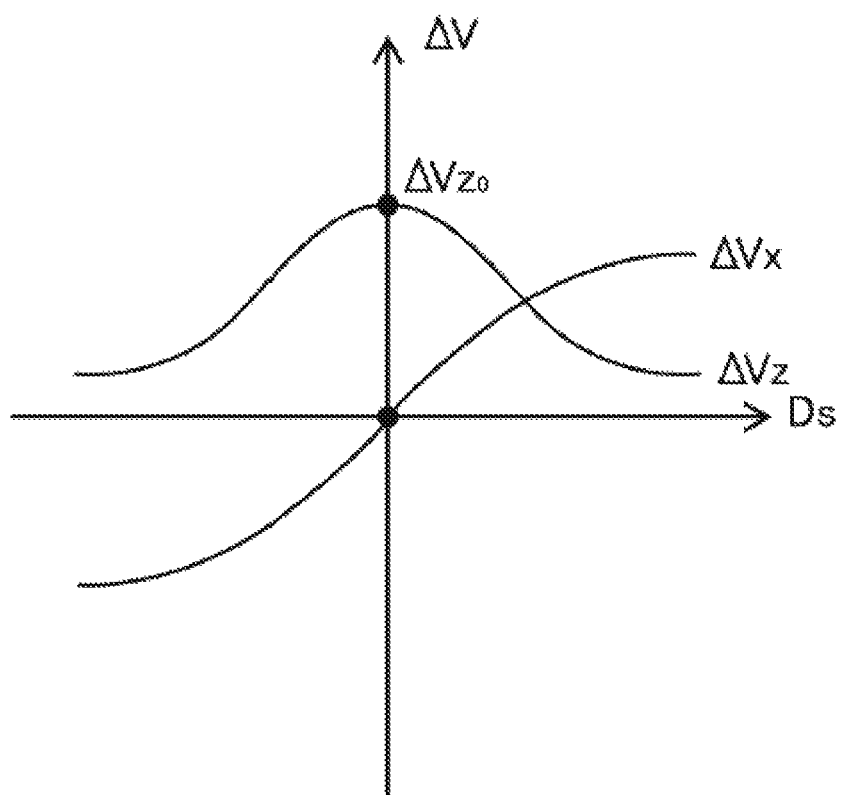

FIG. 11A and FIG. 11B are a schematic front view showing a state of a magnetic field formed by the magnet 2A and a graph showing output values outputted from differential circuits $15_x$ and $15_z$, respectively.

When the sensor IC 1 and the magnet 2A are not displaced relatively to each other as shown in FIG. 10, the magnet 2A is positioned right above the sensor IC 1 as shown in FIG. 11A.

In this case, a left Hall element group of the sensor IC 1 detects a magnetic flux density having a positive value in the x direction and a negative value in the z direction, while a right Hall element group detects a magnetic flux density having a positive value in the x direction and a positive value in the z direction. The absolute values of the magnetic flux densities in the x direction detected by the respective Hall element groups are the same, and the absolute values of the magnetic flux densities in the z direction detected by the respective Hall element groups are the same. Therefore, as shown in FIG. 11B, an output value $\Delta V_x$, which is outputted from the differential circuit 15$_x$ and proportional to $\Delta B_x$, becomes 0, and an output value $\Delta V_z$, which is outputted from the differential circuit 15$_z$ and proportional to $\Delta B_z$, becomes the maximum value $\Delta V_{z0}$.

Moreover, the output value $\Delta V_x$, which is outputted from the differential circuit 15$_x$ and proportional to $\Delta B_x$, and the output value $\Delta V_z$, which is outputted from the differential circuit 15$_z$ and proportional to $\Delta B_z$, are as shown in FIG. 11B according to the displacement of the magnet 2A.

Advantages of the Second Embodiment

According to the second embodiment described above, the influence of disturbance noise on the magnetic field to be detected is reduced like the first embodiment even when the magnetization direction Dm is set to the x direction, and a detectable range of the displacement can be made wider than a pitch $d_p$ of the magnetic detection elements even though a monopole magnet is used.

Other Embodiments

It should be noted that the invention is not limited to the above embodiments, and various modifications can be made in a scope without departing from the gist of the invention.

Moreover, the sensors and magnets of the first and second embodiments described above are examples, and a change can be made into a different combination by appropriately selecting each of these in a scope that the functions of the position detection are not impaired and the gist of one embodiment of the invention is not changed.

What is claim is:

1. A displacement detection device, comprising:
a magnet which is displaced in one direction, is rod-shaped and having a longitudinal direction that forms a predetermined angle with the one direction; and
a sensor including magnetic detection element groups, each of the detection element groups comprises at least two magnetic detection elements which detect a magnetic flux density of a magnetic field formed by the magnet in directions orthogonal to the one direction, the magnetic detection elements are arranged in pairs with a predetermined interval, and the sensor outputs a difference between outputs of the pair of the magnetic detection element groups, wherein:
the sensor comprises: magnetic detection elements, which are included in the magnetic detection element groups and have a sensitive direction in a first direction orthogonal to the one direction; and magnetic concentrators which convert a magnetic flux in a second direction orthogonal to the one direction and the first direction into a magnetic flux in the first direction.

2. The displacement detection device according to claim 1, wherein:
the sensor detects a magnetic flux density in the first direction by adding outputs of the magnetic detection elements included in the magnetic detection element groups and detects a magnetic flux density in the second direction by calculating a difference between the outputs of the magnetic detection elements included in the magnetic detection element groups.

3. The displacement detection device according to claim 1, wherein:
the magnet has a magnetization direction in a direction orthogonal to the one direction.

4. The displacement detection device according to claim 2, wherein:
the magnet has a magnetization direction in a direction orthogonal to the one direction.

5. A displacement detection device, comprising:
a magnet which is displaced in one direction, is rod-shaped and having a longitudinal direction that forms a predetermined angle with the one direction; and
a sensor including magnetic detection element groups, each of the detection element groups comprises at least two magnetic detection elements which detect a magnetic flux density of a magnetic field formed by the magnet in directions orthogonal to the one direction, the magnetic detection elements are arranged in pairs with a predetermined interval, and the sensor outputs a difference between outputs of the pair of the magnetic detection element groups, wherein:
the sensor comprises: magnetic detection elements, which are included in the magnetic detection element groups and have a sensitive direction in a first direction orthogonal to the one direction; and magnetic concentrators which convert a magnetic flux in a second direction orthogonal to the one direction and the first direction into a magnetic flux in the first direction.

6. The displacement detection device according to claim 5, wherein:
the sensor detects a magnetic flux density in the first direction by adding outputs of the magnetic detection elements included in the magnetic detection element groups and detects a magnetic flux density in the second direction by calculating a difference between the outputs of the magnetic detection elements included in the magnetic detection element groups.

7. The displacement detection device according to claim 5, wherein:
the magnet has a magnetization direction in a direction orthogonal to the one direction.

8. The displacement detection device according to claim 5, wherein:
the magnet has a magnetization direction in a direction orthogonal to the one direction.

9. The displacement detection device according to claim 5, wherein:
the magnet has a magnetization direction in a direction orthogonal to the one direction.

10. A displacement detection device, comprising:
a magnet which is displaced in one direction, is rod-shaped and having a longitudinal direction that forms a predetermined angle with the one direction; and
a sensor including magnetic detection element groups, each of the detection element groups comprises at least two magnetic detection elements which detect a magnetic flux density of a magnetic field formed by the magnet in directions orthogonal to the one direction, the magnetic detection elements are arranged in pairs with a predetermined interval, and the sensor outputs a difference between outputs of the pair of the magnetic detection element groups, wherein:

the sensor comprises: magnetic detection elements, which are included in the magnetic detection element groups and have a sensitive direction in a first direction orthogonal to the one direction; and magnetic concentrators which convert a magnetic flux in a second direction orthogonal to the one direction and the first direction into a magnetic flux in the first direction; and detects a magnetic flux density in the first direction by adding outputs of the magnetic detection elements included in the magnetic detection element groups and detects a magnetic flux density in the second direction by calculating a difference between the outputs of the magnetic detection elements included in the magnetic detection element groups.

11. The displacement detection device according to claim 10, wherein:

the magnet has a magnetization direction in a direction orthogonal to the one direction.

12. The displacement detection device according to claim 10, wherein:

the magnet has a magnetization direction in a direction orthogonal to the one direction.

13. The displacement detection device according to claim 10, wherein:

the magnet has a magnetization direction in a direction orthogonal to the one direction.

* * * * *